United States Patent [19]

Cook et al.

[11] Patent Number: 4,810,826

[45] Date of Patent: Mar. 7, 1989

[54] LIQUID-PHASE PROCESS FOR THE OXYIODINATION OF NAPHTHALENE

[75] Inventors: Steven L. Cook; George G. Mayfield, both of Kingsport, Tenn.

[73] Assignee: Eastman Kodak Company, Rochester, N.Y.

[21] Appl. No.: 169,554

[22] Filed: Mar. 17, 1988

[51] Int. Cl.$^4$ ............................................... C07C 17/15
[52] U.S. Cl. .................................. 570/203; 570/206; 570/208
[58] Field of Search ................ 570/203, 206, 208, 207

[56] References Cited

U.S. PATENT DOCUMENTS

| | | | |
|---|---|---|---|
| 3,363,010 | 1/1968 | Schwartzenbek | 570/203 |
| 4,746,758 | 3/1988 | Rules et al. | 570/203 |

FOREIGN PATENT DOCUMENTS

| | | | |
|---|---|---|---|
| 0181790 | 5/1986 | European Pat. Off. | 570/203 |
| 0183579 | 6/1986 | European Pat. Off. | 570/203 |
| 0077631 | 5/1982 | Japan | 570/203 |
| 159496 | 3/1964 | U.S.S.R. | 570/203 |

OTHER PUBLICATIONS

JP 58077830 (WPI Acc No: 83-59518K/25, Derwent).
SU 453392 (WPI Acc No: 75-45621W/27, Derwent).
*Journal of the American Chemical Society*, 39, 435 (1917).
*Journal of Chemical Education*, 48, 508 (1971).
Uemura, Noe, and Okano, *Bulletin of Chemical Society of Japan*, 47, 147, (1974).
JP 57077631 (WPI Acc No: 82-51282E/25, Derwent).
JP 59219241 (WPI Acc No: 85-022839/04, Derwent).

*Primary Examiner*—Werren B. Lone
*Attorney, Agent, or Firm*—Charles R. Martin; William P. Heath, Jr.

[57] ABSTRACT

A process for the liquid-phase oxyiodination of naphthalene which comprises (1) preparing a liquid-phase feed mixture of iodine and naphthalene and/or iodine, naphthalene and iodonaphthalenes, and (2) contacting the feed mixture with a zeolite catalyst in the presence of a gaseous source of oxygen to produce an iodinated naphthalene mixture and water, and (3) removing water from the iodinated naphthalene mixture.

12 Claims, No Drawings

LIQUID-PHASE PROCESS FOR THE OXYIODINATION OF NAPHTHALENE

The present invention relates to a process for the liquid-phase iodination of naphthalene over a zeolite catalyst.

It has long been desired to be able to derivatize aromatic compounds and in particular, condensed ring aromatic compounds in commercially attractive quantities since many of these compounds possess properties which would fill long sought needs. In particular, substituted benzene and naphthalene carboxylic acids or esters are particularly desired for use in the manufacture of polyesters which would have excellent properties when fabricated into films, bottles or coatings. However, known techniques for producing these carboxylic acids and esters are very expensive and impractical for commercial exploitation.

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Pat. No. 453392 and by Data and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508 (1971). The use of metal halogenides to catalyze iodination has been suggested by Uemura, Noe, and Okano in the *Bulletin of Chemical Society of Japan*, 47, 147, (1074). The concept of direct iodination of benzene in the gas phase over the zeolite 13X has been suggested in Japanese Patent Publication No. 82/77631 in the absence of any oxidizing agent.

Ishida and Chono in Japanese Kokai No. 59/219241 have suggested a technique for oxyiodinating benzene over a very acidic zeolite catalyst having a silica to alumina (SiO2:Al2O3) ratio of greater than 10. In this technique benzene is reacted with iodine in the presence of oxygen to produce iodinated benzene. According to this disclosure approximately 96% of the benzene which is converted is converted to the iodinated form. However, the remaining benzene is oxidized to carbon dioxide and other combustion products resulting in the loss of valuable starting material.

Subsequent to the present invention, Paparatto and Saetti disclosed in European Patent Applications Nos. 181,790 and 183,579 techniques for oxyiodination of benzene over zeolite catalysts. European Patent Application No. 181,790 suggests the use of ZSM-5 and ZSM-11 type zeolites which has been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type or Y type of zeolite in non-acid form. According to No. 183,579 the X or Y zeolites have to be used in the form exchanged with monovalent, bivalent or trivalent cations and in particular with alkaline or rare earth cations. The techniques of Nos. 181,790 and 183,579 prepare the monoiodobenzene in selectivities in excess of 90% and only distinctly minor amounts of the diiodobenzene compounds.

The gas phase oxyiodination of aromatic compounds, particularly benzene and naphthalene, can be carried out continuously by feeding a mixture of the aromatic compound, iodine, and air over a heated bed of zeolite catalyst as noted above. However, there are several disadvantages to practicing this reaction in the gas phase. The naphthalene and recycled iodonaphthalenes must be vaporized, and thus more energy input is required. Also, the reaction is exothermic and temperature control of this exothermic reaction is difficult to practice in the gas phase. Accordingly, a need exists for a liquid-phase oxyiodination process for the iodination of aromatic compounds, particularly naphthalene.

In summary this process of this invention comprises
 (a) preparing a liquid-phase feed mixture of iodine and naphthalene or iodine and an iodonaphthalene,
 (b) contacting the feed mixture with a zeolite catalyst in the presence of a gaseous oxygen source to produce an iodinated naphthalene mixture and water, and
 (c) removing water from the iodinated naphthalene mixture.

In accordance with the first step of the process a liquid-phase mixture of iodine and naphthalene or iodine, naphthalene and iodonaphthalenes are prepared. The iodonaphthalene can have either one, two or three iodine atoms bonded to the ring and can be in any position. Preferably there are two iodine atoms bonded in the para position. In a most preferred embodent the mixture is comprised of iodine, naphthalene and diodonaphthalene.

The mixture is prepared by conventional techniques such as pumping the materials into a common line under conditions to create good mixing. Although the invention is not limited as to the amount of iodine broadly the feed mixture can comprise about 1 to 35, more preferably 5 to 15 weight percent iodine, based on the weight of the feed mixture.

The second step of the process comprises contacting the feed mixture with a zeolite catalyst in the presence of a gaseous oxygen source to produce an iodinated naphthalene mixture and water.

The type of zeolite catalyst which may be utilized in the present process is not critical so long as the zeolites have a pore or cavity size at least equal to about the apparent size of the naphthalene molecule. Benzene as well as naphthalene have an apparent ring size of about 5-9 A and this is the lower limit on the pore size of the zeolite catalyst which is useful. If the naphthalene molecules cannot enter into the pore of the zeolite catalyst then only very little oxyiodination will occur. The zeolite catalyst may be in the acid or non-acid form. Preferred zeolites are the X and Y-type zeolites with X-type zeolites being most preferred.

Specifically preferred zeolite catalysts are those disclosed in copending Ser. Nos. 912,806, filed Sept. 9, 1986; 029,896, filed Mar. 25, 1987; 029,959, filed Mar. 25, 1987; 029,897, filed Mar. 25, 1987; 029,898, filed Mar. 25, 1987; and 070,249, filed July 6, 1987. The specifications of these copending applications are incorporated herein by reference for a more complete description of the catalysts.

The zeolite catalyst may contain additional cations which have been incorporated into the zeolite catalyst to modify its activity. Suitable cations include alkali, alkaline earth and transition metal cations as well as rare earth cations.

The modifying cations may be incorporated into the zeolite catalyst by any conventional means such as for example simple ion exchange or other methods well known to those in the art. Ion exchange is generally accomplished by contacting the zeolite with an aqueous solution of a salt of the desired modifier cation. The number of times the zeolite is contacted with the ion solution determines the degree of incorporation of the desired modifier cation. The preferred cation is potassium.

The catalyst activity and reactivity are dependent on the amount of water which remains in the liquid phase in the reactor and course, dependent on the size of the particular reactor which is utilized. Purge rates can generally vary from about 50 to 2,000 cc/minute for the reactor size noted above, but it is preferred to operate at a purge rate of about 50 to 1,000 cc/minute and most preferred to operate at 100 to 600 cc/minute to optimize the space-time yield.

The gaseous oxygen source may be air, enriched air, oxygen or a mixture of these with an diluent such as CO, $CO_2$, nitrogen, or argon gases.

While any amount of oxygen may be incorporated in the inert gas, it is preferred that the gaseous oxygen source contain from 5% to 30% oxygen in the diluent with the remaining 95% to 70% being an inert gas.

The second step of the process may be conducted in any type of reactor in which the temperature and pressure can be controlled to maintain the feed mixture in the liquid phase and at the same time allow the continuous removal of the water of reaction in the gas phase in accordance with the third step. The reactor design should allow sufficient mass transfer of water to maintain the desired activity of the zeolite catalyst. Suitable reactors include tubular reactors, as well as tank reactors and fluidized bed reactors. The present method may be performed on a batch basis provided sufficient mass transfer of water away from the catalyst can be effected. When continuous operation is desired, a tubular reactor containing the zeolite catalyst, i.e., a "trickle-bed reactor" is preferred.

As a practical consideration, the reactor and associated structural components should be constructed of a material which is resistant to the attack by iodine and water which are corrosive. The reactor and associated parts may be constructed of conventional materials which are resistant to attach by iodine and water. Hastelloy has been found to be a suitable construction material although other conventional materials may also be used.

In general, the reactor is operated at temperatures from about 150° to 400° C. A preferred temperature range is from 280° to 320° C.

Operating pressures can generally vary from above atmospheric pressure to about 1,000 psig, with preferred operating pressures of from 15 to 1,000 psig.

The third step of this process is to remove the water from the iodinated naphthalene mixture. Since the first and second steps of the process of the present invention are operated at temperatures and pressures at which the feed mixture is in the liquid phase, the water of reaction is automatically volatilized into the gas phase and thereby removed from the iodinated naphthalene mixture. Typically the water is eliminated from the reactor with unreacted oxygen and inert gas. Under certain reaction conditions, iodine may also be volatilized and appear in the gas phase. Under these conditions, the iodine may be recovered from the off-gas by conventional scrubbing techniques.

The process of the present invention produces an iodinated naphthalene mixture which contains monoiodonaphthalenes as well as diiodonaphthalenes. When diiodonaphthalenes, i.e., 2,6- and 2,7-diiodonaphthalene are the desired products, the initial product mixture can be recycled to the liquid-phase oxyiodination reactor to increase the relative amount of diiodonaphthalenes present in the product mixture. If necessary, additional iodine may be added to the recycled product stream. In addition to simply recycling the initial product stream one or more times, numerous other recycle options are possible with the present process. For example, mixtures of naphthalene and/or monoiodonaphthalenes and diiodonaphthalenes may be added to the recycle stream from other sources. A typical source would be the crude product from a gas phase oxyiodination reactor, although naphthalene and iodinated naphthalenes from any source could be added to the reactant stream. In general, the addition of supplemental amounts of naphthalenes and iodonaphthalenes requires that additional iodine be added to the reactant feed stream as well.

Alternatively, the recycle operations can be conducted in stages using several oxyiodination reactors connected in series. Iodine is added to the product stream from each oxyiodination reactor before the product stream enters the next iodination reactor in the series. In this manner, sufficient iodine is present to effectively increase the relative concentration of diiodonaphthalenes in each successive stage of processing. The product mixture exiting the final reactor may be separated into the desired diiodonaphthalenes and the unreacted starting materials recycled to one or more of the preceeding reactors.

The present reaction may be run as a batch process with isolation of the diiodonaphthalene components from the batch product mixture or may be run as a continuous or semi-continuous process with continuous isolation of the diiodonaphthalenes and recycle of the unreacted naphthalene and monoiodonaphthalenes to the reactor. Separation of the diiodonaphthalenes may be accomplished by any suitable separation means, such as crystallization or distillation.

Practice of this invention yields a product which has a 2,6-diiodonaphthalene/2,7-diiodonaphthalene ratio higher than that which is obtained via optimized conditions using a gas-phase oxyiodination reaction.

Other features of the invention will become apparent in the course of the following descriptions of exemplary embodiments which are given for illustration of the invention and are not intended to be limiting thereof.

EXAMPLES

Example 1

A 198.0-gram quantity of molten naphthalene was mixed with 2.0 grams of iodine. The mixture was pumped to a tubular reactor 30 cm in length having an internal diameter of 1.12 cm at the rate of 50 cc/hour. The reactor was operated at 280° C. and a head pressure of 500 psig of 10% oxygen in nitrogen, and the off-gas purge rate was 1000 cc/minute. A sample of the product, taken after 3 hours of operation, had the following composition: Weight percent 2-iodonaphthalene=1.3, percent 1-iodonaphthalene=0.2. No diiodonaphthalenes were detected.

Example 2

The weight percent iodine in the naphthalene feed was varied from two to six. The results of all runs are summarized in Table I.

TABLE I
PRODUCT ANALYSES (AVERAGED) AND SPACE-TIME YIELD OF 2-IODONAPHTHALENE

| Reactor Temperature | Weight Percentage Iodine | Percent 2-Isomer | Percent 1-Isomer | Percent 2,6-Isomer |
|---|---|---|---|---|
| 280 | 1 | 1.3 | 0.2 | — |
| 280 | 2 | 2.2 | 0.3 | 0.05 |
| 280 | 4 | 3.7 | 0.6 | 0.40 |
| 300 | 4 | 6.6 | 1.1 | 0.35 |
| 310 | 6 | 8.1 | 0.8 | 0.60 |

Example 3

The concentration of iodine and the naphthalene-iodine feed rates were held constant at 5% and 50 cc/hour, respectively, while the conditions of head pressure, temperature, and off-gas purge rate were varied. The feed gas was 10% oxygen in nitrogen.

The head pressure was varied from 350 psig to 700 psig, the reactor temperature from 290° to 320° C., and the off-gas purge rate from 200 cc/minute to 1000 cc/minute. A typical analysis of product from these runs showed 84.40% naphthalene, 7.52% 2-iodonaphthalene, 1.62% 1-iodonaphthalene, 0.27% 2,6-diiodonaphthalene (2,6-DIN), and 0.05% other diiodonaphthalenes. The 2-iodonaphthalene/1-iodonaphthalene isomer ratio was found to be about 5:1 throughout these experiments. The space-time yield (STY), in grams per liter-hour, of 2-iodonaphthalene was calculated for each run, and the results are summarized in Table II.

TABLE II

| Temperature | Pressure | Off-Gas Purge Rate | STY of 2-Iodonaphthalene |
|---|---|---|---|
| 290 | 350 | 200 | 143 |
| 290 | 350 | 1000 | 65 |
| 290 | 700 | 200 | 167 |
| 290 | 700 | 1000 | 73 |
| 320 | 350 | 200 | 127 |
| 320 | 350 | 1000 | 85 |
| 320 | 700 | 200 | 109 |
| 320 | 700 | 1000 | 89 |

Example 4

Three identical runs were made at 525 psig of 10% oxygen in nitrogen, 305° C., 600 cc/minute off-gas purge rate, in naphthalene at 50 cc/hour feed rate. The 2-iodonaphthalene space-time yield was found to be 100, 112, and 90.

Example 6

A mixture of 1- and 2-monoiodonaphthalenes (MIN) were fed to the unit. The reaction conditions and feed rates were identical to those used for the recycle experiments in Example 5. The reactor was initially fed with a mixture of 1-MIN and 2-MIN and 10% (w/v) iodine. No iodine breakthrough was seen during this run. The next run was performed as above but with 15% iodine in the feed. The larger amount of iodine resulted in iodine breakthrough in both the vapor exiting the reactor and in the product, but the yield of 2,6-DIN was higher. The results are summarized in Table IV.

TABLE IV

|  | START. MAT. | 10% Iodine | 15% Iodine |
|---|---|---|---|
| Naphthalene | 0.14 | 0.78 | 0.22 |
| 2-Iodonaphthalene | 75.86 | 59.95 | 54.98 |
| 1-Iodonaphthalene | 21.93 | 19.52 | 19.25 |
| 2,6 Diiodonaphthalene | 0.73 | 14.83 | 18.42 |
| 2,7 Diiodonaphthalene | 0.44 | 2.69 | 3.22 |
| Other | 0.12 | 1.62 | 2.62 |

Example 7

The reactor was fed with a mixture of distilled mono and diiodonaphthalenes. Twenty percent of this feed consisted of material from distillations of the crude product of a gas phase oxyiodination reactor. This material was combined with 1-iodo and 2-iodonaphthalene feed from Example 6. The composite was analyzed and showed no detectable naphthalene, 62.21% 2-iodonaphthalene, 17.80% 1-iodonaphthalene, 10.08% 2,6-diiodonaphthalene, 4.36% 2,7-diiodonaphthalene, and 4.91% other diiodonaphthalenes. The reactor was operated for a total of 5 hours at 350 psig head pressure with 10% oxygen in nitrogen, 305° C., 8.04 weight percent iodine at a iodonaphthalene/iodine feed rate of 60 cc/hour, and 600 cc/minute off-gas purge rate. The product analyzed 0.11% naphthalene, 43.45% 2-iodonaphthalene, 15.43% 1-iodonaphthalene, 26.94% 2,6-diiodonaphthalene, 6.70% 2,7-diiodonaphthalene, and 7.78% other diiodonaphthalenes. The product collection rate was 90.6 g/hour and represented a 2,6-diiodonaphthalene space-time yield of 547 g/L-hour.

Example 8

The feed gas was switched to air and the head pressure reduced to 160 psig. All other conditions were the same as for Example 7. The reaction product analyzed 0.14% naphthalene, 48.61% 2-iodonaphthalene, 16.20% 1-iodonaphthalene, 23.13% 2,6-diiodonaphthalene, 4.62% 2,7-diiodonaphthalene, and 5.54% other diiodonaphthalenes.

Obviously, numerous modifications and variations of the present invention are possible in light of the above teachings. It is therefore to be understood that within the scope of the appended claims, the invention may be practiced otherwise than as specifically described herein.

We claim:
1. A process comprising
   (a) preparing a liquid-phase feed mixture of iodine and naphthalene or iodine, naphthalene, and an iodonaphthalene,
   (b) producing an iodinated naphthalene mixture and water, a portion of which is in the gas phase, by contacting the feed mixture with a zeolite catalyst at a temperature in the range of about 150° to 400° C. and a pressure in the range of 15 to 1,000 psig, and in the presence of a gaseous oxygen source, and
   (c) removing the water which is in the gas-phase from the iodinated naphthalene mixture by purging the iodinated naphthalene mixture with the gaseous oxygen source moving at a rate in the range of about 50 to 2,000 cc/minute.

2. The process of claim 1 wherein the feed mixture comprises a mixture of iodine, naphthalene, iodonaphthalene and diiodonaphthalenes.

3. The process of claim 2 wherein the feed mixture comprises about 1 to 35 weight % iodine.

4. The process of claim 3 wherein the feed mixture comprises about 5 to 15 weight % iodine.

5. The process of claim 1 wherein the zeolite is an X-type zeolite.

6. The process of claim 5 wherein the zeolite is in the potassium form.

7. The process of claim 1 wherein said gaseous oxygen source comprises air, enriched air or oxygen.

8. The process of claim 7 wherein the gaseous oxygen source comprises a mixture of 5 to 30 weight % oxygen and 95 to 70 weight % inert gas.

9. The process of claim 1 wherein step (b) is conducted at a temperature from about 250° to 350° C.

10. The process of claim 9 wherein the temperature is about 280° to 320° C.

11. The process of claim 1 wherein step (b) is conducted in a trickle-bed reactor.

12. A process comprising
(a) preparing a liquid-phase feed mixture of iodine, naphthalene, iodonaphthalene and diiodonaphthalenes which contains about 5 to 15 weight % iodine,
(b) producing an iodinated naphthalene mixture and water, a portion of which is in the gas phase, by contacting the feed mixture with an X-type zeolite in the potassium form in a trickle-bed reactor in the presence of a gaseous oxygen source composed of a mixture of a 5 to 30 weight % oxygen and 95 to 70 weight % of an inert gas at a pressure in the range of about 15 to 1000 psig at a temperature of about 280° to 320° C., and
(c) removing the water in the gas-phase from the iodinated naphthalene mixture by purging the iodinated naphthalene mixture with the gaseous oxygen source moving at a rate of about 100 to 600 cc/minute.

* * * * *